United States Patent [19]

Yamamoto et al.

[11] Patent Number: 4,657,704
[45] Date of Patent: Apr. 14, 1987

[54] PRODUCTION OF AMINOALKYLSULFONIC ACIDS

[75] Inventors: Isamu Yamamoto, Zushi; Yoshiaki Noguchi, Yokohama; Kouzou Iwasaki; Kenichi Arai, both of Mobara, all of Japan

[73] Assignee: Mitsui Toatsu Chemicals, Incorporated, Tokyo, Japan

[21] Appl. No.: 824,947

[22] PCT Filed: Sep. 8, 1982

[86] PCT No.: PCT/JP83/00301

§ 371 Date: May 2, 1984

§ 102(e) Date: May 2, 1984

[87] PCT Pub. No.: WO84/00958

PCT Pub. Date: Mar. 15, 1984

Related U.S. Application Data

[63] Continuation of Ser. No. 610,298, May 2, 1984, abandoned.

[30] Foreign Application Priority Data

Sep. 8, 1982 [JP] Japan .................. 57-155284
Jul. 19, 1983 [JP] Japan .................. 58-130160

[51] Int. Cl.$^4$ .................................. C07C 143/02
[52] U.S. Cl. .................................... 260/513 B
[58] Field of Search ........................... 260/513 B

[56] References Cited

FOREIGN PATENT DOCUMENTS 1229542 12/1966 Fed. Rep. of Germany ... 260/513 B

OTHER PUBLICATIONS

Gilbert, "Sulfonation and Related Reactions", (1965), p. 137.
Gilbert, "Sulfonation and Related Factors", (1965), pp. 148 and 149.
J. Chem. Soc., (1936), pp. 191 and 192.

Primary Examiner—Alan Siegel
Attorney, Agent, or Firm—Fisher, Christen & Sabol

[57] ABSTRACT

Disclosed herein is a process for preparing with a high yield an aminoalkylsulfonic acid represented by the following general formula:

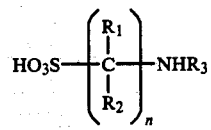

wherein $R_1$, $R_2$ and $R_3$ are each a hydrogen atom, an alkyl group having 1–3 carbon atoms or a hydroxyl-containing alkyl group having 1–3 carbon atoms and n stands for an integer of 2 or 3, which process comprises reacting a sulfite with a halogenated alkylamine represented by the following general formula:

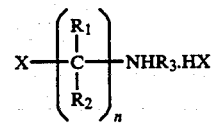

wherein X means a chlorine, bromine or iodine atom, and $R_1$, $R_2$, $R_3$ and n have the same meanings as defined above by adding the halogenated alkylamine little by little either continuously or intermittently over a certain period of time to a heated aqueous solution of the sulfite.

The yield may be increased further when, after the addition of the halogenated alkylamine, the reaction is carried out by raising the reaction temperature stepwise in 2–5 stages while limiting the reaction time and temperature-raising range in each stage to 0.5–4 hours and 10°–20° C.

4 Claims, No Drawings

PRODUCTION OF AMINOALKYLSULFONIC ACIDS

This application is a continuation of application Ser. No. 610,298 filed 5-2-84 now abandoned.

DESCRIPTION

1. Technical Field:

This invention relates to a process for preparing aminoalkylsulfonic acids at a low production cost and with a high yield.

2. Background Art:

Aminoalkylsulfonic acids are useful compounds as intermediate raw materials for pharmaceutical products, surfactants, pH buffers, etc. Among such aminoalkylsulfonic acids, 2-aminoethylsulfonic acid is an extremely useful compound because it per se has such pharmacological effects as detoxification effect, fatigue-relieving effect and nourishing and tonifying effect.

The following processes have heretofore been known as preparation processes of aminoalkylsulfonic acids:

(1) To react sulfur dioxide gas and water with ethyleneimine (Japanese Patent Publication Nos. 23007/1965 and 16807/1972);

(2) To react ethylene chloride with sodium sulfite to form sodium 2-chloroethylsulfonate, with which a liquid mixture of anhydrous ammonia or a 27% aqueous solution of ammonia and ammonium carbonate, or an alkylamine is heated under elevated pressure to react them together [Ind. Eng. Chem., 39, 906 (1947)];

(3) To react a hydroxylalkylsulfonic acid with ammonia or an alkylamine under elevated pressure (U.S. Pat. Nos. 1,932,907 and 1,999,614);

(4) To oxidize 2,2-disubstituted thiazolidine with hydrogen peroxide (Japanese Patent Laid-open No. 26654/1982);

(5) To react 2-aminoethanol sulfate with sodium sulfite (J. Chem. Soc., 1943, 4); and (6) To react a hydrogen halide salt of a 2-halogenoethylamine with a sulfite [(Ind. Eng. Chem., 39, 906 (1947); and J. Am. Chem. Soc., 58, 191 (1936)].

These conventional processes are however accompanied by such serious problems as will be mentioned below. The process (1) involves some serious hazards from the viewpoint of safety since it uses, as raw materials, ethyleneimine which has extremely strong toxicity and carcinogenicity and is expensive and sulfur dioxide which induces chest pain, cough and dyspnea when it is inhaled. Moreover, the reaction is an extremely exothermic and thus involves a great problem from the viewpoint of reaction control upon effecting the reaction on an industrial scale. In the process (2) or (3), it is necessary to conduct the reaction by heating ammonia or an alkylamine under elevated pressure. The processes (2) and (3) are each accompanied with another drawback that its industrial application requies extremely expensive production facilities. On the other hand, the process (4) requires to use hydrogen peroxide which is very dangerous in handling it and, accordingly, involves a safety problem. Besides, the operation becomes irksome because ketones, which are by-produced, must be recovered and recycled. In the case of each of the processes (5) and (6), there is a merit that the raw materials are easy to handle because they are safe compounds. However, they were still accompanied by such problems as will be referred to below. In the process (5), the reaction between the sulfate and sodium sulfite is extremely slow and requires heating over a long period of time. Moreover, the sulfate per se is a compound liable to hydrolysis. Due to the hydrolysis of the sulfate upon undergoing a reaction with sodium sulfite, monoethanolamine is unavoidably by-produced. In addition to an extremely low yield, the process (5) is accompanied by a variety of problems such as the separation and recovery of the thus by-produced monoethanolamine. Although the process (6) can achieve a relatively high yield, for example, 80% in the case of 2-bromoethylamine, the yield is still insufficient to employ the process (6) on an industrial scale. In order to make the yield still higher, it is indispensable to use the sulfite to large excess, thereby raising another problem as to the separation and recovery of the sulfite. In the case of 2-chloroethylamine, the process (6) can provide a yield still lower than the process (5) and cannot thus be considered as an industrial preparation process.

As has been described in detail, none of the conventional processes was considered to be a satisfactory process, because they are accompanied by serious drawbacks with respect to their raw materials per se or, where raw materials are safe substances, yields are low or troublesome post treatments are required.

The present inventors have carried out an extensive investigation on the process (6) employing raw materials which are extremely safe and easy to handle, with a view toward developing an industrially-applicable process.

As a result, it has been found that three types of reactions, which are represented respectively by the following reaction formulae, are occurring in the reaction system of a sulfite and a halogenated alkylamine.

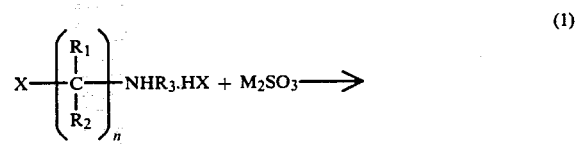

(1)

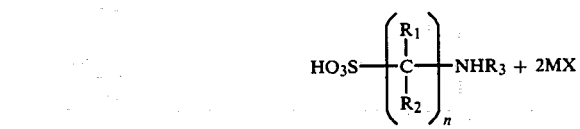

(2)

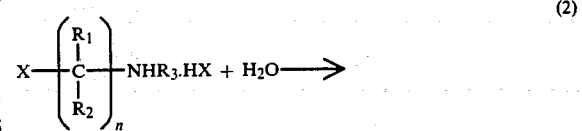

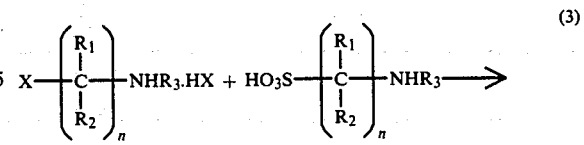

(3)

-continued

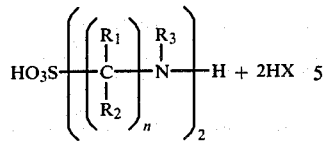

(In the above reaction formulae, $R_1$, $R_2$, $R_3$, X, n and M have the same meanings as will be defined in the general formula (I) and (II) later in this specification.)

In the above-described conventional process in which a sulfite and a halogenated alkylamine are reacted to each other under reflux, the hydrolysis reaction represented by the reaction formula (2) takes place simultaneously besides the principal reaction represented by the reaction formula (1). Thus, the yield of the intended compound is very low. The reaction which is represented by the reaction formula (3) and has not been known so far is seemed to cause the yield to drop further, because a large excess amount of a halogenated alkylamine is present at elevated temperatures relative to an aminoalkylsulfonic acid formed in accordance with the reaction formula (1) and the reaction system is under conditions extremely ready to trigger the reaction of the reaction formula (3). The present inventors have then made a further intensive investigation with a view toward developing a process capable of suppressing the side reactions represented respectively by the reaction formulae (2) and (3). As a result, it has been found that the side reactions can be suppressed by selecting the reaction conditions suitably, leading to the completion of this invention.

DISCLOSURE OF THE INVENTION

The present invention relates to a process for preparing an aminoalkylsulfonic acid represented by the general formula (III):

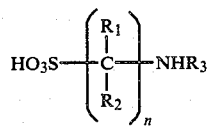
(III)

wherein $R_1$, $R_2$ and $R_3$ are each a hydrogen atom, an alkyl group having 1-3 carbon atoms or a hydroxyl-containing alkyl group having 1-3 carbon atoms and may be either the same or different and n stands for an integer of 2 or 3, which process comprises reacting a sulfite represented by the general formula (I):

$$M_2SO_3 \quad (I)$$

wherein M denotes an alkali metal or ammonium with a halogenated alkylamine represented by the general formula (II):

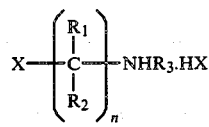
(II)

wherein X means a chlorine, bromine or iodine and $R_1$, $R_2$, $R_3$ and n have the same meanings as defined above by adding the halogenated alkylamine little by little either continuously or intermittently over a certain period of time to an aqueous solution of the sulfite which aqueous solution has been heated to a temperature of at least 50° C.

According to the process of this invention, a desired aminoalkylsulfonic acid can be prepared with a high yield while using materials, which are safe and easy to handle, and suppressing side reactions.

BEST MODE FOR CARRYING OUT THE INVENTION

As a sulfite useful in the practice of the process of this invention, may be mentioned sodium, potassium or ammonium sulfite which is readily available. On the other hand, exemplary halogenated alkylamines may embrace 2-haloethylamines, N-methyl-2-haloethylamines, N-ethyl-2-haloethylamines, N-(2-hydroxyethyl)-2-haloethylamines, N-propyl-2-haloethylamines, 3-halopropylamines, N-methyl-3-halopropylamines, 2-halo-propylamines, N-(2-hydroxypropyl)-2-halopropylamines, 1-methyl-2-haloethylamines, 2-halobutylamines, etc. In these compounds, the halogens may be either one of chlorine, bromine and iodine. These compounds may be prepared with ease by processes known per se in the art, namely, (1) by reacting thionyl chloride with an alkanolamine [German Offenlegungsschrift No. 27 01 215 (1978)], (2) by causing a hydrohalogenic acid to act on an alkanolamine, or in the like manner.

In the present invention, the preparation process of an aminoalkylsulfonic acid may be proceeded in the following manner. Namely, an aqueous solution of a sulfite is heated in advance, to which a halogenated alkylamine is added, either as it is or in the form of an aqueous solution, little by little either continuously or intermittently over a certain period of time (hereinafter called "portioned addition" or "addition in portions"). Then, the reaction mixture is heated with stirring at the same temperature for a predetermined period of time or is heated stepwise to complete the reaction.

Many of the hydrohalide salts of halogenated alkylamines are hygroscopic. Accordingly, it is better to add them as aqueous solutions from the viewpoint of handling readiness.

The concentration of the aqueous solution of the sulfite may preferably range from 10% to saturation. Although the reaction may still proceed sufficiently even if the concentration is lower than 10%, use of such a low concentration requires a large reaction apparatus when producing the aminoalkylsulfonic acid on an industrial scale. Hence, such a low concentration is not economical. It is unnecessary to add the sulfite beyond saturation into a slurry state, because satisfactory effects can be achieved at concentrations lower than saturation. On the other hand, the concentration of an aqueous solution of the hydrohalide salt of a halogenated alkylamine, which aqueous solution is added in portions, may preferably range from 10% to saturation as measured in term of the hydrohalide salt. Although the reaction may still proceed at a concentration lower than 10%, such a low concentration requires large production facilities and is thus uneconomical when carrying out the reaction on an industrial scale.

The halogenated alkylamine is added, as mentioned above, in portions to the aqueous solution of the sulfite in the present invention. The rate of addition may preferably be 0.1-1.0 mole/hr. on average of the halogenated alkylamine per mole of the sulfite. The time period of addition may vary in accordance with the temperature at the time of addition and the molar ratio of the sulfite and halogenated alkylamine to be reacted. The time period of addition may be made shorter as the temperature increases or the molar ratio becomes greater. However, the time period of addition may generally be preferred to be from 30 minutes to 10 hours.

Any rates of addition exceeding 1.0 mole/hr. or any time periods of addition shorter than 30 minutes are not preferred because the effects of the portioned addition cannot be brought about to any significant extent. On the other hand, it is not preferred to add at any rates lower than 0.1 mole/hr. or over any time periods in excess of 10 hours, because such manner of addition requires longer reaction time but is unable to bring about any additional effects despite of such longer reaction time. The temperature of the aqueous sulfite solution may preferably range from 50° C. to its boiling point, or especially from 50° C. to 60° C. when adding the halogenated alkylamine in portions. Although the reaction may still proceed even if the temperature is lower than 50° C., use of such a low temperature requires longer reaction time and is thus not preferred. After the portioned addition, the heating may be effected by heating the reaction mixture at the same temperature in the range of from 50° C. to the boiling point for a predetermined period of time. However, it is preferred to raise the temperature of the reaction mixture stepwise to carry out the reaction. The expression "to raise the temperature of the reaction mixture stepwise" as used herein means that the temperature of the reaction mixture is raised by a predetermined extent with a predetermined interval and the reaction mixture is then held at the thus-raised temperature for a certain period of time and these procedures are then repeated intermittently. More specifically, the temperature range from the temperature at the time point of adding the halogenated alkylamine in portions to the boiling point is divided into 2-5 sections and the temperature of the reaction mixture is raised stepwise by 10°-20° C. with an interval of 0.5-4 hours. It is not different substantially from the usual continuous temperature-raising procedure to raise the temperature in a time period shorter than 0.5 hour, leading to a lowered yield presumably due to occurrence of side reactions. It is not preferred to hold the reaction mixture at the same temperature over a time period longer than 4 hours, because the reaction time becomes unduly long.

The heating time may vary depending on the temperature. It is however preferred to heat for a period of from 30 minutes to 10 hours. When changing the reaction temeprature stepwise, it is preferred to heat the reaction mixture for 1-10 hours. Any heating time periods shorter than 30 minutes are not preferred because the reaction has not yet been brought to completion and the yield is still low. On the other hand, it is unnecessary to heat for any time periods beyond 10 hours because satisfactory effects can be obtained with a heating period of 10 hours or shorter.

In the present invention, the sulfite may be employed in an amount 1-3 times the equivalent of the halogenated alkylamine. When the reaction mixture is heated stepwise, the sulfite may be use in an amount 1-1.5 times, or especially 1.05-1.25 times the equivalent of the halogenated alkylamine. If the sulfite should be used in any amounts less than the equivalent of the halogenated alkylamine, a significant reduction will occur in yield for the possible reason that the salt of the excess halogenated alkylamine undergoes undesirous side reactions. It is, on the other hand, unnecessary to use the sulfite in any amounts more than 3 times the equivalent of the halogenated alkylamine, because satisfactory effects can be obtained with the use of the sulfite in an amount not more than 3 times the halogenated alkylamine.

The separation of the aminoalkylsulfonic acid from the liquid reaction mixture may be carried out by any method known per se in the art after completion of the reaction. For example, water is removed by distillation from the liquid reaction mixture. Then, hydrochloric acid is is added to dissolve the aminoalkylsulfonic acid, followed by the removal of the resulting inorganic salt through its filtration. The resultant hydrochloric acid solution which contains the aminoalkylsulfonic acid is concentrated. The intended product can be caused to deposit as crystals by adding ethanol to the concentrate. The intended product can thus be collected by filtration.

An aminoalkylsulfonic acid can thus be prepared with a high yield by using only raw materials, which are extremely safe and thus easy to handle and are also inexpensive, in accordance with the preparation process of this invention.

The invention will hereinafter be described in further detail by the following Examples.

EXAMPLE 1

In a one-liter 5-necked flask equipped with a stirrer, reflux condenser, dropping funnel, $N_2$-blowing port and thermometer, 26.8 g (0.2 mole) of ammonium sulfite monohydrate and 107.3 g of water were added and the contents were stirred under an $N_2$ gas stream to dissolve the former in the latter.

Placed in the dropping funnel was a solution which had been prepared by dissolving 59.76 g (0.2 mole) of 2-iodoethylamine hydroiodide in 239.04 g of water. The aqueous solution of ammonium sulfite was heated to 50° C. in the flask, to which the aqueous solution of 2-iodoethylamine hydroiodide was dropped from the dropping funnel in the course of 9 hours. After completion of the dropwise addition, the reaction mixture was continuously stirred for additional 9 hours, also, at 50° C. The above reaction was always carried out under the $N_2$ gas stream.

After completion of the reaction, water was removed under reduced pressures. Then, 120 ml of conc. hydrochloric acid was added to the residue so as to dissolve the resultant taurine. Thereafter, insoluble inorganic salts were removed by filtration. The filtrate was concentrated to 100 ml, to which 100 ml of ethanol was added to cause taurine to appear as crystals. The crystals were separated by filtration. Yield: 23.3 g (93%). Its IR and NMR data were in conformity with those of its corresponding standard.

Elementary analysis: Calculated for $C_2H_7NO_3S$: C, 19.19; H, 5.64; N, 11.19; S, 25.62. Found: C, 19.21; H, 5.71; N, 11.18; S, 25.37.

EXAMPLE 2

In a 300-ml, 5-necked flask equipped with a stirrer, reflux condenser, dropping funnel, $N_2$-blowing port and thermometer, 47.5 g (0.3 mole) of anhydrous potassium sulfite and 47.5 g of water were added. The contents were stirred under an $N_2$ gas stream to dissolve anhydrous potassium sulfite in water. In addition, the dropping funnel was charged with a solution which had been prepared by dissolving 41.0 g (0.2 mole) of 2-bromoethylamine hydrobromide in 41.0 g of water.

The aqueous solution of potassium sulfite was heated to 70° C. in the flask, to which the aqueous solution of 2-bromoethylamine hydrobromide was added dropwise over 5 hours from the dropping funnel.

After completion of the dropwise addition, the reaction mixture was heated to 80° C., where the stirring of the reaction mixture was continued for 4 hours. The above reaction was always carried out under the $N_2$ gas stream.

After completion of the reaction, the isolation of taurine was carried out in the same manner as in Example 1.

Yield: 23.8 g (95%). Its IR and NMR data were coincided with those of its corresponding standard.

Elementary analysis: Calculated for $C_2H_7NO_3S$: C, 19.19; H, 5.64; N, 11.19; S, 25.62. Found: C, 19.10; H, 5.56; N, 11.01; S, 25.77.

EXAMPLE 3

Added to a 500-ml, 5-necked flask equipped with a stirrer, reflux condenser, dropping funnel, $N_2$-blowing port and thermometer were 50.4 g (0.4 mole) of anhydrous sodium sulfite and 178.1 g of water. The contents were stirred under an $N_2$ gas stream to dissolve anhydrous sodium sulfite in water. Furthermore, the dropping funnel was charged with a solution which had been prepared by dissolving 23.2 g (0.2 mole) of 2-chloroethylamine hydrochloride in 5.8 g of water.

The aqueous solution of sodium sulfite in the flask was heated to a temperature at which water was allowed to reflux. To the thus-heated aqueous solution of sodium sulfite, the aqueous solution of 2-chloroethylamine hydrochloride was dropped in the course of 40 minutes from the dropping funnel. After completion of the dropwise addition, the contents of the flask were stirred for further 40 minutes, also, at the water-refluxing temperature. The above reaction was always carried out under the $N_2$ gas stream.

The isolation of taurine after completion of the reaction was conducted in the same manner as in Example 1.

Yield: 24.3 g (97%). Its IR and NMR data were in conformity with those of its corresponding standard.

Elementary analysis: Calculated for $C_2H_7NO_3S$: C, 19.19; H, 5.64; N, 11.19; S, 25.62. Found: C, 19.15; H, 5.56; N, 11.03; S, 25.70.

EXAMPLE 4

A 500-ml, 5-necked flask, which was equipped with a stirrer, reflux condenser, powder-charging port, $N_2$-blowing port and thermometer, was charged with 75.6 g (0.6 mole) of anhydrous sodium sulfite and 267.2 g of water. Under an $N_2$ gas stream, anhydrous sodium sulfite was dissolved in water. The resultant solution was heated to 80° C., to which 23.2 g (0.2 mole) of 2-chloroethylamine hydrochloride was added in portions over 3 hours. After completion of the addition, the stirring was continued for 3 hours at the same temperature. The above reaction was always conducted under the $N_2$-gas stream.

After completion of the reaction, the isolation of taurine was conducted in the same manner as in Example 1.

Yield: 24.0 g (96%). Its IR and NMR were in conformity with those of its corresponding standard.

Elementary analysis: Calculated for $C_2H_7NO_3S$: C, 19.19H, 5.64; N, 11.19; S, 25.62. Found: C, 19.25; H, 5.74; N, 11.01; S, 25.82.

EXAMPLE 5

In a 500-ml, 5-necked flask equipped with a stirrer, thermometer, dropping funnel, reflux condenser and $N_2$-blowing port, were added 50.4 g (0.4 mole) of anhydrous sodium sulfite and 178 g of water. The contents were stirred under an $N_2$ gas stream to dissolve anhydrous sodium sulfite in water.

The dropping funnel was charged with 55.1 g of an 80% aqueous solution (0.38 mole) of 2-chloroethylamine hydrochloride.

The aqueous solution of sodium sulfite in the flask was heated to 55° C., at which temperature the aqueous solution of 2-chloroethylamine hydrochloride was dropped over 4 hours from the dropping funnel. The dropping rate was 0.24 mole/hr. on average of 2-chloroethylamine hydrochloride per mole of sodium sulfite.

After the dropwise addition, the contents were stirred at 55° C. for 1 hour. Then, the heating was intensified in such a way that the reaction was carried out for 2 hours at 65° C., for 2 hours at 80° C., for 2 hours at 90° C., and for 1 hour at the boiling point (105° C.). The above reaction was always effected under the $N_2$ gas stream.

After completion of the reaction, water was removed under reduced pressures and 150 ml of conc. hydrochloric acid was added to the residue to dissolve taurine which had occurred.

Insoluble inorganic salts were filtered off and washed with conc. hydrochloric acid 5 times (20–25 ml of conc. hydrochloric acid per each washing). The filtrate and washings were combined together and then concentrated to about 100 ml under reduced pressures. Then, 100 ml of ethanol was added to the concentrate to cause taurine to deposit. The resulting mixture was filtered to isolate taurine. Taurine was then dried under reduced pressures.

Yield: 46.6 g (98.1%). Its IR and NMR data were inconformity with those of its corresponding standard.

The following is the result of an elementary analysis made on the above-prepared taurine.

Elementary analysis: Calculated for $C_2H_7NO_3S$: C, 19.19; H, 5.64; N, 11.19; S, 25.62. Found: C, 19.28; H, 5.81; N, 11.06; S, 25.41.

EXAMPLE 6

A 300-ml, 5-necked flask, which was equipped with a stirrer, thermometer, dropping funnel, reflux condenser and $N_2$-blowing port, was charged with 34.8 g (0.22 mole) of anhydrous potassium sulfite and 35 g of water. The contents were stirred under an $N_2$ gas stream to dissolve anhydrous potassium sulfite in water. Then, the dropping funnel was charged with 82 g of a 50% aqueous solution (0.2 mole) of 2-bromoethylamine hydrobromide.

The aqueous solution of potassium sulfite was heated to 55° C., at which temperature the aqueous solution of 2-bromoethylamine hydrobromide was dropped over 5 hours from the dropping funnel. The dropping rate was 0.18 mole/hr. on average per mole of potassium sulfite.

After completion of the dropwise addition, the heating was intensified so as to conduct the reaction at 65° C. for 2 hours, at 80° C. for 2 hours and at 90° C. for 1 hour. The above reaction was always conducted under the N₂ gas stream.

After completion of the reaction, the post treatment was carried out in the same manner as in Example 5 to obtain taurine.

Yield: 24.6 g (98.2%). Its IR and NMR data were in conformity with those of its corresponding standard, and the following was the result of its elementary analysis.

Elementary analysis: Calculated for $C_2H_7NO_3S$: C, 19.19; H, 5.64; N, 11.19; S, 25.62. Found: C, 19.23; H, 5.74; N, 11.15; S, 25.38.

EXAMPLE 7

Placed in a 300-ml, 5-necked flask equipped with a stirrer, thermometer, reflux condenser, powder-charging port and N₂-blowing port was 132.3 g of a 20% aqueous solution (0.21 mole) of sodium sulfite. The aqueous solution was then heated to 55° C. under an N₂ gas stream, to which 23.2 g (0.2 mole) of 2-chloroethylamine hydrochloride was added in portions over 2 hours. The addition rate was 0.48 mole/hr. on average per mole of sodium sulfite. After the addition, the reaction mixture was heated at 70° C. for 2 hours, at 85° C. for 2 hours, and at 100° C. for 1 hour to effect the reaction. After the reaction, the post treatment was carried out in the same manner as in Example 5, thereby obtaining taurine. Its IR and NMR data were in conformity with those of its corresponding standard.

Yield: 24.4 g (97.6%).

Elementary analysis: Calculated for $C_2H_7NO_3S$: C, 19.19; H, 5.64; N, 11.19; S, 25.62. Found: C, 19.28; H, 5.78; N, 11.24; S, 25.51.

EXAMPLES 8-13

Using apparatus similar to that used in Example 5, the raw materials given in Table 1 were reacted under the conditions also given in Table 1.

After reactions, the post treatments were carried out respectively in the same manner as in Example 5 to obtain the results summarized in Table 1.

The reaction products were identified by IR and NMR analyses.

TABLE 1

| | Conditions & results | | | | |
|---|---|---|---|---|---|
| | Aqueous | Aqueous solution | Addition | | |
| Example | sulfite solution | of halogenated alkylamine | temp. (°C.) | time (hrs.) | rate* mole/hr. |
| Example 8 | Ammonium sulfite monohydrate - 26.8 g (0.20 mole); water - 107 g | 2-Iodoethylamine hydroiodide - 59.8 g (0.20 mole); water 239 g | 50 | 9 | 0.11 |
| Example 9 | Anhydrous potassium sulfite - 38.0 g (0.24 mole); water - 57 g | N—Methyl-2-chloroethylamine hydrochloride - 26.0 g (0.20 mole); water - 60 g | 55 | 3 | 0.28 |
| Example 10 | Anhydrous sodium sulfite - 31.5 g (0.25 mole); water - 250 g | 3-Chloropropylamine hydrochloride - 26.0 g (0.20 mole); water - 8 g | 50 | 4 | 0.20 |
| Example 11 | Anhydrous sodium sulfite - 27.7 g (0.22 mole); water - 160 g | 2-Chlorobutylamine hydrochloride - 28.8 g (0.20 mole); water - 28 g | 60 | 1 | 0.91 |
| Example 12 | Anhydrous sodium sulfite - 37.8 g (0.30 mole); water - 172 g | N—(2-Hydroxyethyl)-2-chloroethylamine hydrochloride - 32.0 g (0.20 mole); water - 20 g | 60 | 2 | 0.33 |
| Example 13 | Anhydrous sodium sulfite - 26.5 g (0.21 mole); water - 94 g | 2-Chloropropylamine hydrochloride - 26.0 g (0.20 mole); water - 26 g | 55 | 2 | 0.48 |

| | Conditions & results | | | Elementary analysis, % | | | |
|---|---|---|---|---|---|---|---|
| Example | Reaction conditions | Product | Yield | C | H | N | S |
| Example 8 | 70° C. × 2 hrs. 90° C. × 1 hr. | Taurine | 24.1 g (96.4%) | Calculated: 19.19 Found: 19.32 | 5.64 5.81 | 11.19 11.13 | 25.62 25.57 |
| Example 9 | 65° C. × 2 hrs. 80° C. × 3 hrs. 90° C. × 1 hr. | N—Methyltaurine | 27.2 g (97.7%) | Calculated: 25.89 Found: 25.73 | 6.52 6.47 | 10.06 10.18 | 23.04 23.15 |
| Example 10 | 65° C. × 1 hr. 75° C. × 2 hrs. 85° C. × 1 hr. 95° C. × 0.5 hr. 105° C. × 0.5 hr. | 3-Aminopropanesulfonic acid | 26.9 g (96.6%) | Calculated: 25.89 Found: 25.94 | 6.52 6.59 | 10.06 10.17 | 23.04 23.11 |
| Example 11 | 80° C. × 2 hrs. 95° C. × 3 hrs. | β-Ethyltaurine | 29.7 g (96.9%) | Calculated: 31.36 Found: 31.22 | 7.24 7.17 | 9.14 9.06 | 20.93 20.81 |
| Example 12 | 75° C. × 0.5 hr. | N—(2- | 32.4 g | Calculated: | | | |

TABLE 1-continued

| | | | | | | | | |
|---|---|---|---|---|---|---|---|---|
| | 90° C. × 0.5 hr.<br>100° C. × 0.5 hr. | Hydroxy-<br>ethyl)-2-<br>aminoethane-<br>sulfonic<br>acid | (95.7%) | Calculated:<br>28.40<br>Found:<br>28.33 | 6.55<br>6.71 | 8.28<br>8.36 | 18.95<br>19.07 | |
| Example 13 | 75° C. × 2 hrs.<br>95° C. × 1 hr. | β-Methyl-<br>taurine | 27.0 g<br>(97.0%) | Calculated:<br>25.89<br>Found:<br>25.81 | 6.52<br>6.65 | 10.06<br>10.13 | 23.04<br>22.97 | |

*per mole of sulfite.

COMPARATIVE EXAMPLE

A 500-ml, 4-necked flask, which was fitted with a stirrer, thermometer, reflux condenser and $N_2$-blowing port, was charged with 50.4 g (0.4 mole) of anhydrous sodium sulfite and 178 g of water. The contents were stirred under an $N_2$ gas stream to dissolve anhydrous sodium sulfite in water. To the thus-formed solution, 46.4 g of a 50% aqueous solution (0.2 mole) of 2-chloro-ethylamine hydrochloride was added. The flask was heated over oil bath and the reaction was effected for 8 hours under reflux.

After completion of the reaction, the post treatment was carried out in the same manner as in Example 1, thereby obtaining taurine.

Yield: 18.4 g (73.6%). Its IR and NMR data were in conformity with those of its corresponding standard. Its elementary analysis data are as follows:

Elementary analysis: Calculated for $C_2H_7NO_3S$: C, 19.19; H, 5.64; N, 11.19; S, 25.62. Found: C, 19.28; H, 5.76; N, 11.05; S, 25.37.

We claim:

1. Process for preparing an aminoalkylsulfonic acid represented by the general formula (III):

  (III)

wherein $R_3$ is a hydrogen atom or an alkyl group having 1 to 3 carbon atoms and n stands for an integer of 2 or 3, which process comprises reacting, under a nitrogen atmosphere, a sulfite represented by the general formula (I):

  (I)

wherein M denotes an alkali metal or ammonium, with a chloroalkylamine represented by the general formula (II):

  (II)

wherein $R_3$ and n have the same meanings as defined above, by adding the chloroalkylamine either continuously or intermittently to an aqueous solution of the sulfite which aqueous solution contains the sulfite in an amount of 1 to 1.5 times the equivalent of the chloroalkylamine and has been heated to a temperature of 50° to 60° C., and the reaction temperature, after the addition of the chloroalkylamine, is raised stepwise so as to complete the reaction.

2. The process according to claim 1 wherein the chloroalkylamine is added at a rate of 0.1 to 1 mole/hour on average per mole of the sulfite, the reaction temperature is raised stepwise in 2 to 5 stages after the addition of the chloroalkylamine, the reaction time and temperature-raising range in each stage are 0.5 to 4 hours and 10° to 20° C. respectively, and the reaction temperature in the last stage is below the boiling point of the reaction system.

3. The process according to claim 1 wherein the chloroalkylamine is 2-chloroethylamine, N-methyl-2-chloroethylamine or 3-chloropropylamine.

4. The process according to claim 1 wherein the sulfite is sodium, potassium or ammonium sulfite.

* * * * *